(12) United States Patent
Shelley et al.

(10) Patent No.: US 8,338,787 B1
(45) Date of Patent: Dec. 25, 2012

(54) SYSTEM AND METHOD FOR RESIN THICKNESS MEASUREMENT

(75) Inventors: Paul H. Shelley, Lakewood, WA (US); Gregory J. Werner, Puyallup, WA (US); Paul G. Vahey, Seatle, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 13/151,147

(22) Filed: Jun. 1, 2011

(51) Int. Cl.
*G01J 5/02* (2006.01)
(52) U.S. Cl. .................................................. 250/341.7
(58) Field of Classification Search .......... 250/330–335, 250/336.1–336.2, 338.1–338.5, 339.01–339.15, 250/340, 341.1–341.8
See application file for complete search history.

(56) References Cited

U.S. PATENT DOCUMENTS

| 6,903,339 | B2 | 6/2005 | Shelley et al. |
| 7,223,977 | B2 | 5/2007 | Shelley et al. |

FOREIGN PATENT DOCUMENTS

| EP | 1011086 A2 * | 6/2000 |
| JP | 11077805 A * | 3/1999 |

OTHER PUBLICATIONS

Shelley, Jr. et al., "Resin Detection System," USPTO U.S. Appl. No. 13/418,064, filed Mar. 12, 2012, 68 pages.

* cited by examiner

*Primary Examiner* — Kiho Kim
(74) *Attorney, Agent, or Firm* — Yee & Associates, P.C.

(57) ABSTRACT

A system for surface resin thickness measurement on a fiber reinforced polmer composite includes a holding fixture configured to match a contour of a composite part in which a resin thickness is to be measured, a plurality of infrared measurement sensors in the holding fixture which can be moved along the surface to create a map of the surface to be measured, a computer-based data acquisition system interfacing with the plurality of infrared measurement sensors and calibration software supporting the data acquisition system.

21 Claims, 4 Drawing Sheets

SYSTEM AND METHOD FOR RESIN THICKNESS MEASUREMENT

TECHNICAL FIELD

The disclosure generally relates to quantitative measurement of resin thickness on the surface of a polymer composite structure. More particularly, the disclosure relates to a system and method for quantitative measurement of resin thickness on the contoured surface of a polymer composite structure using near-infrared (IR) spectroscopy and to measure coating thickness on composite or metal surfaces.

BACKGROUND

Fiber reinforced polmer composite structures contain successive layers of fiber and polymer resin. During fabrication of a composite, a wrinkle in one ply of fiber material can propagate through adjoining layers to the surface, resulting in a localized region of thick resin, or a "resin pocket". It is useful to measure the resin pocket dimensions as a means of quantifying surface wrinkle which can potentially impact the performance of a structure. Current ultrasonic non-destructive testing (NDT) methods cannot reliably detect resin pockets less than about 0.070 to 0.080 inches (70 to 80 mils) deep. Such measurements have poor accuracy and require close contact with the part. Visual inspection for resin pockets in carbon fiber reinforced plastic (CFRP) composite structures is especially difficult, due to the poor reflectivity of black carbon fibers. A non-destructive technique is needed to determine resin pocket dimensions greater than 0.0150 inches (15 mils) deep in composite structures. Such information can then be used to identify wrinkles as an indication of quality of the structure.

SUMMARY

The disclosure is generally directed to a system for resin thickness measurement. An illustrative embodiment of the system includes a holding fixture configured to match a contour of a resin the thickness of which is to be measured, a plurality of infrared measurement sensors in the holding fixture, a computer-based data acquisition system interfacing with the plurality of infrared measurement sensors and calibration software supporting the data acquisition system.

In some embodiments, the system for resin thickness measurement may include a holding fixture having a measuring surface configured to match a contour of a resin the thickness of which is to be measured; a plurality of infrared measurement sensors in the holding fixture and interfacing with the measuring surface; a computer-based data acquisition system interfacing with the plurality of infrared measurement sensors; and calibration software supporting the data acquisition system and adapted to correlate a level of absorbance of infrared energy at each of the plurality of infrared measurement sensors to a known calibration for resin thickness.

The disclosure is further generally directed to a method for resin thickness measurement. An illustrative embodiment of the method includes providing a holding fixture configured to match a contour of a resin the thickness of which is to be measured and having an array of infrared measurement sensors in the holding fixture, exposing the resin of the composite structure to near infrared energy at each of the infrared measurement sensors, detecting a level of absorbance of infrared energy at each of the infrared measurement sensors and correlating a level of absorbance from each of the infrared measurement sensors to a known calibration for resin thickness.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary or the following detailed description.

Figure 2:
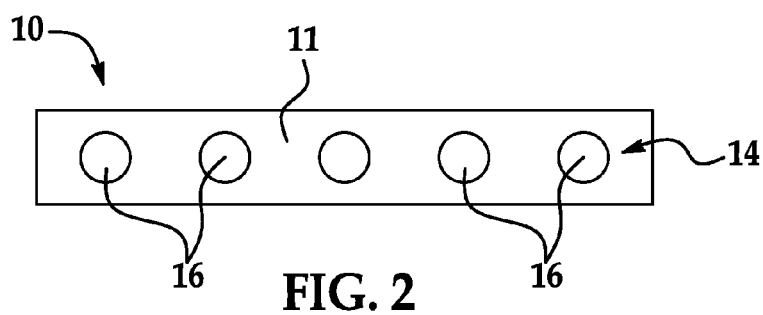
FIG. 2 is a top view of the IR sensor assembly, more particularly illustrating a one-dimensional line array of IR measurement sensors in the assembly.
Figure 3:
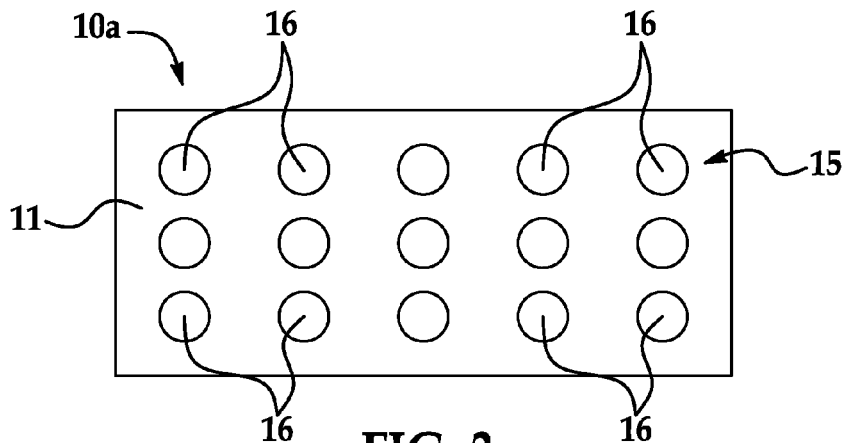
FIG. 3 is a top view of the IR sensor assembly, more particularly illustrating an alternative two-dimensional grid array of the IR measurement sensors in the assembly.
Figure 4:
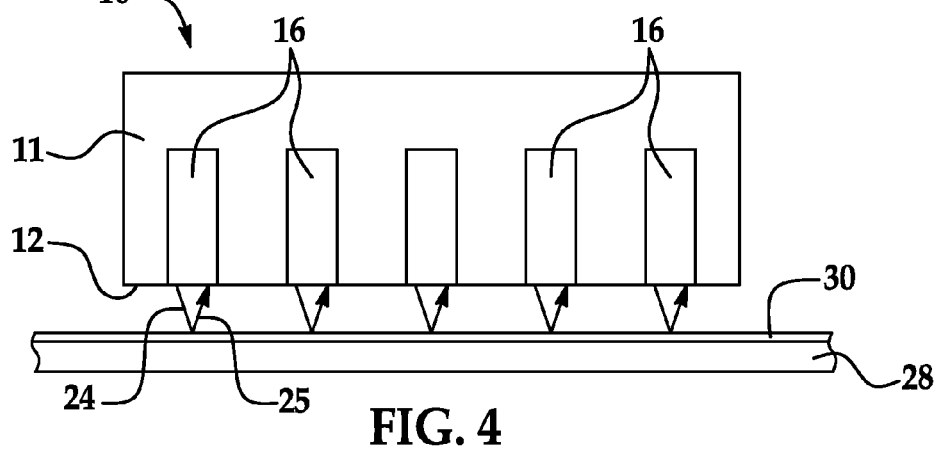
FIG. 4 is a sectional view of the IR sensor assembly, more particularly illustrating IR beams emitted from the respective IR measurement sensors against a flat or planar resin surface on a composite structure in exemplary application of the system.

Referring initially to FIGS. 1-7, an illustrative embodiment of the system for resin thickness measurement, hereinafter system, is generally indicated by reference numeral 1. The system 1 may include an IR (infrared) sensor assembly 10 which will be hereinafter described. A computer-based data acquisition system 704 may interface with the IR sensor assembly 10. The data acquisition system 704 may be supported by calibration software 706. As illustrated in FIG. 4 and will be hereinafter described, the system 700 may be adapted to measure the thickness of a resin 30 on a polymer composite structure 28 by analyzing the absorbance of infrared energy directed against the resin 30.

Figure 1:
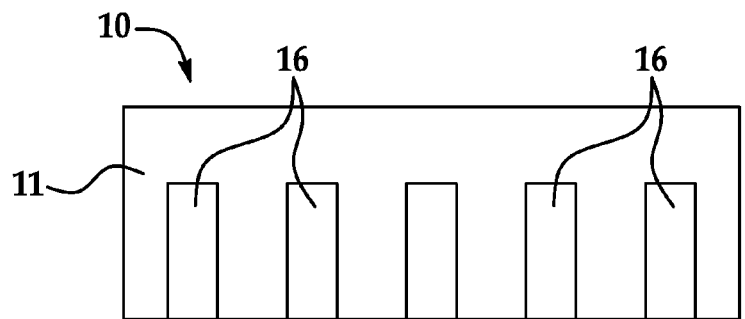
FIG. 1 is a sectional view of an IR sensor assembly of an illustrative embodiment of the system for resin thickness measurement.
Figure 5:
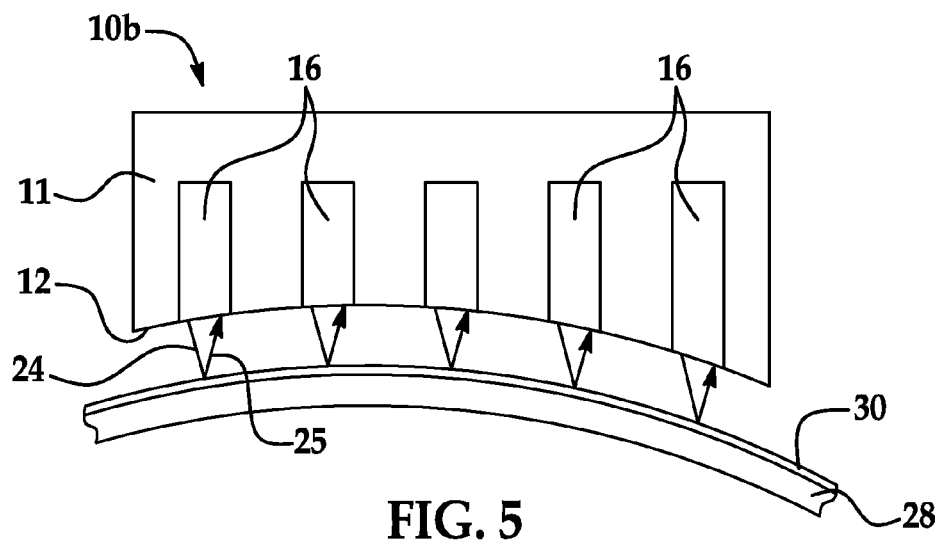
FIG. 5 is a sectional view of an alternative IR sensor assembly, more particularly illustrating IR beams emitted from the respective IR measurement sensors against a convex resin surface on a composite structure in exemplary application of the system.
Figure 6:
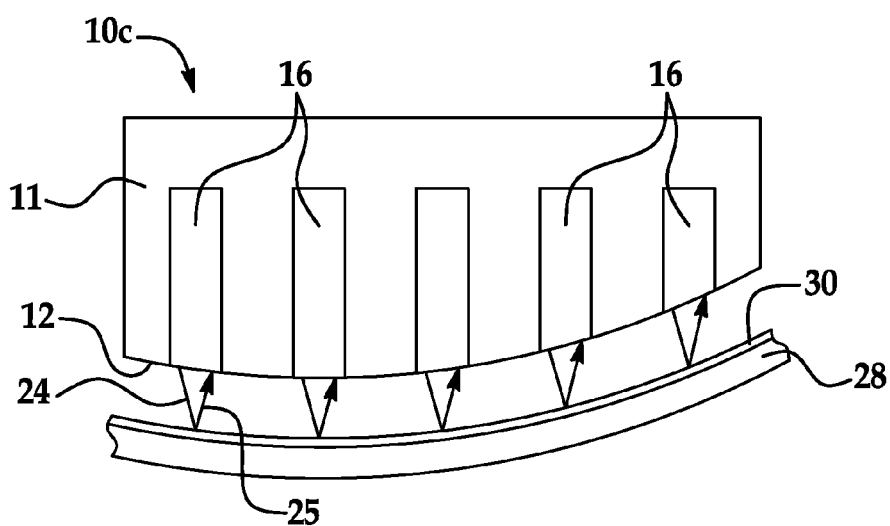
FIG. 6 is a sectional view of another alternative IR sensor assembly, more particularly illustrating IR beams emitted from the respective IR measurement sensors against a concave resin surface on a composite structure in exemplary application of the system.
Figure 7:
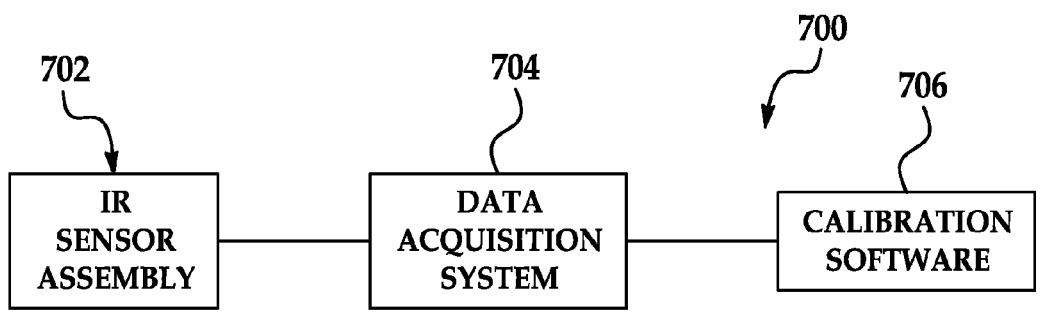
FIG. 7 is a block diagram of an illustrative embodiment of the system for resin thickness measurement.

As shown in FIG. 1, the IR sensor assembly 10 of the system 700 may include a holding fixture 11. The holding fixture 11 may include a measuring surface 12. The measuring surface 12 may generally match the contour of the resin 30 the thickness of which is to be measured using the system 700. For example and without limitation, in FIG. 4, the measuring surface 12 on the holding fixture 11 of the IR sensor assembly 10 may have a generally flat or planar contour to match the flat or planar contour of the resin 30 on the composite structure 28. As shown in FIG. 5, on an alternative IR sensor assembly 10b, the measuring surface 12 may have a generally concave contour to match a convex contour of the resin 30. As shown in FIG. 6, on another alternative IR sensor assembly 10c, the measuring surface 12 may have a generally convex contour to match a concave contour of the resin 30. Alternative configurations of the measuring surface 12 may be possible depending on the contour of the resin 30 the thickness of which is to be measured using the system 700.

As shown in FIG. 1, multiple IR measurement sensors 16 may be provided in the holding fixture 11 of the IR sensor assembly 10. The IR measurement sensors 16 may interface with the measuring surface 12 of the holding fixture 11. The IR measurement sensors 16 may be arranged in any desired pattern in the holding fixture 11. For example and without limitation, as shown in FIG. 2, in some embodiments of the IR sensor assembly 10, the IR measurement sensors 16 may be arranged in a one-dimensional line array 14. As shown in FIG. 3, in other embodiments of the IR sensor assembly 10, the IR measurement sensors 16 may be arranged in a two-dimensional grid array 15.

As illustrated in FIG. 4, each IR measurement sensor 16 in the IR sensor assembly 10 is adapted to emit an incident IR beam 24 against the resin 30 of the composite structure 28. In some embodiments, the incident IR beam 24 may be short wavelength near IR energy in the range of from about 900 nm to about 1700 nm. Each IR measurement sensor 16 may also be adapted to receive a returning IR beam 25 from the resin 30 and measure the absorbance, or the difference in intensity between the incident IR beam 24 and the returning IR beam 25. The absorbance is proportional to the thickness of the resin 30. Accordingly, the data acquisition system 704 is adapted to detect the absorbance measured by each IR measurement sensor 16 in the IR sensor assembly 10. The calibration software 706 may enable the data acquisition system 704 to determine the thickness of the resin 30 by correlating the level of absorbance from each IR measurement sensor 16 to a known calibration standard for resin thickness. Calibration may be based on multivariate spectral analysis of infrared absorbance, multiple peak heights of infrared absorbance or single peak height of infrared absorbance. In some embodiments, the data acquisition system 704 may also be adapted to consolidate or translate the resin thickness data into a single two-dimensional map created by moving an array of IR sensors along the surface of the part.

Referring next to FIG. 4, in exemplary application, the IR sensor assembly 10 of the system 700 is positioned adjacent to a resin 30 on a polymer composite structure 28 preparatory to measuring the thickness of the resin 30. An incident IR beam 24 is emitted from each IR measurement sensor 16 at the measuring surface 12 of the holding fixture 11. In some embodiments, a single (or dual) near IR illumination source may be used for the whole array of near IR sensors. In some embodiments, the incident IR beam 24 may have a wavelength in the range of from about 900 nm to about 1700 nm. The incident IR beam 24 strikes or impinges on the surface of the resin 30 and is transmitted through the resin 30. Passing through the resin 30 changes the incident IR beam 24 into the returning IR beam 25. The IR measurement sensor 16 receives the returning IR beam 25 and transmits data which indicates the absorbance of the IR energy to the data acquisition system 704.

The data acquisition system 704 detects the level of absorbance of the infrared energy at the location of each IR measurement sensor 16 in the IR sensor assembly 10. The calibration software 706 enables the data acquisition system 704 to determine the thickness of the resin 30 by correlating the level of absorbance from each IR measurement sensor 16 to a known calibration for resin thickness. The calibration for resin thickness may be based on multivariate spectral analysis of infrared absorbance, multiple peak heights of infrared absorbance or single peak height of infrared absorbance, for example and without limitation. In some embodiments, the data acquisition system 704 may additionally consolidate or translate resin thickness data at the location of each IR measurement sensor 16 into a single two-dimensional map.

As shown in FIGS. 4-6, it will be appreciated by those skilled in the art that the IR sensor assembly 10 may be selected according to the contour of the measuring surface 12 on the holding fixture 11 such that the measuring surface 12 generally matches the contour of the resin 30 the thickness of which is to be measured. This feature may enhance accuracy of the thickness measurement.

Figure 8:
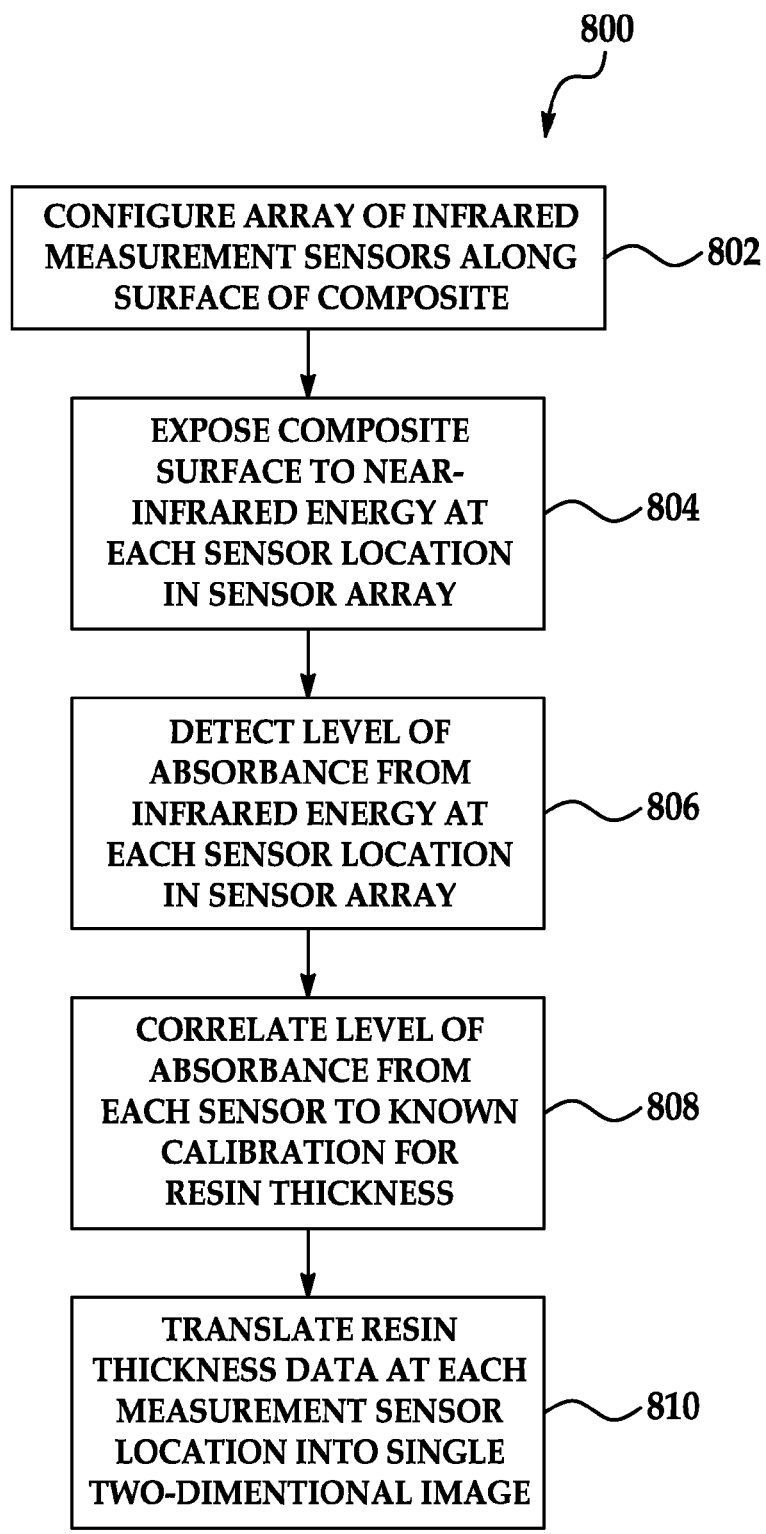
FIG. 8 is a flow diagram which illustrates an illustrative embodiment of a method for resin thickness measurement.

Referring next to FIG. 8, a flow diagram 800 which illustrates an illustrative embodiment of a system for resin thickness measurement is shown. In block 802, a holding fixture is provided. The holding fixture may be configured to match a contour of a resin the thickness of which is to be measured. An array of infrared measurement sensors may be provided in the holding fixture. The holding fixture may be positioned over the composite structure having the resin. The array of infrared measurement sensors may be configured along the surface of composite. In block 804, the resin may be exposed to near-infrared energy at the location of each infrared measurement sensor in the sensor array of the holding fixture. In some embodiments, the near-infrared energy may have a wavelength of from about 900 nm to about 1700 nm.

In block 806, the level of absorbance of the infrared energy at the location of each infrared measurement sensor in the sensor array may be detected. In block 808, the level of absorbance from each infrared measurement sensor may be correlated to a known calibration for resin thickness to determine the thickness of the resin. The calibration may be based on multivariate spectral analysis of infrared absorbance, multiple peak heights of infrared absorbance or single peak height of infrared absorbance, for example and without limitation. In block 810, the resin thickness data at each infrared measurement sensor which was obtained in block 808 may be consolidated or translated into a single two-dimensional image.

It will be appreciated by those skilled in the art that the system and method for resin thickness measurement of the disclosure is particularly suited to measuring resin thickness on the order of 20 to 40 mils. However, thickness outside this range may also be measured. Moreover, the system and method may be used for coating thickness measurements and offers significant advantages for both non-contact readings and imaging of a larger area. For these measurements, the longer IR wavelengths may be more useful (1700-2500 NM near IR or 2.5 to 25 microns mid-IR).

Figure 9:
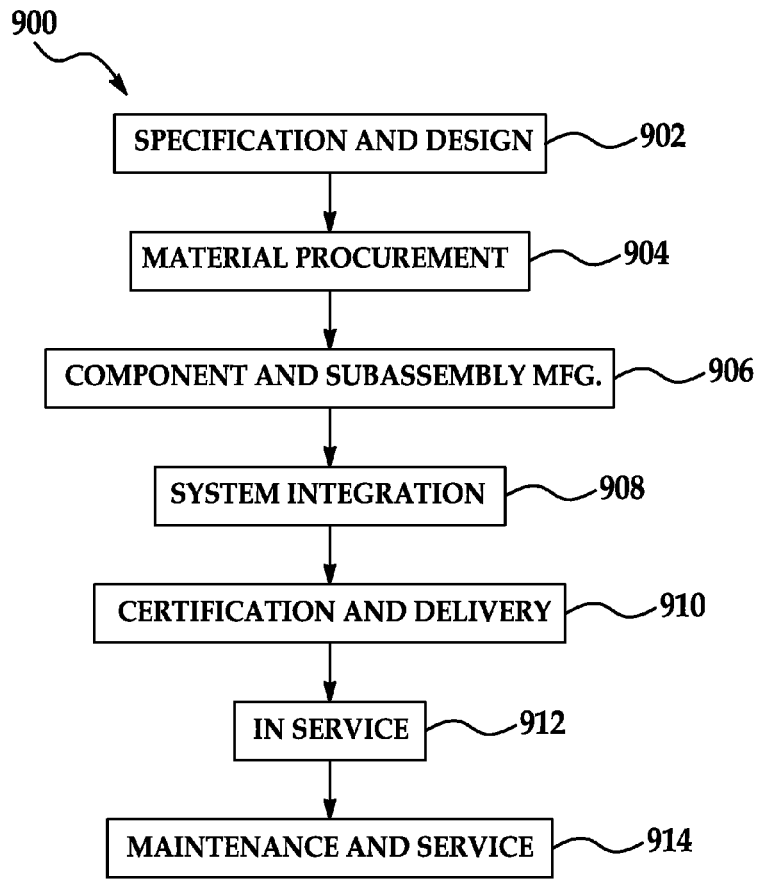
FIG. 9 is a flow diagram of an aircraft production and service methodology.
Figure 10:
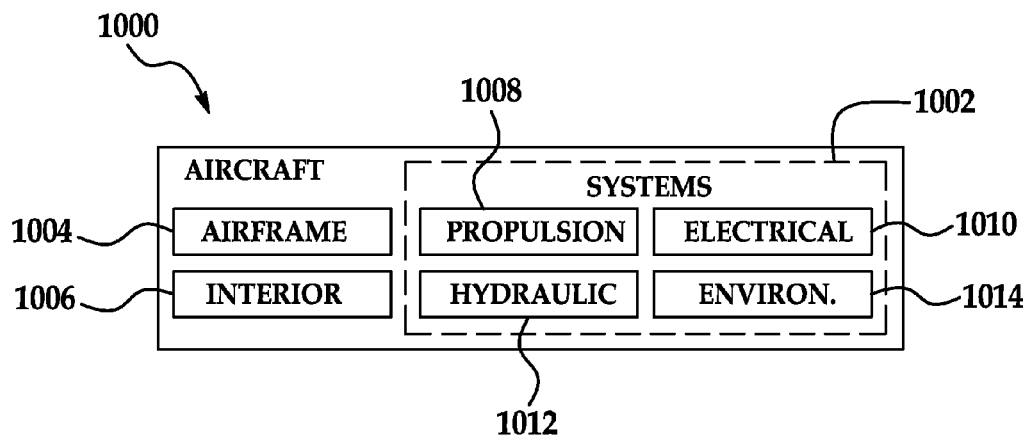
FIG. 10 is a block diagram of an aircraft.

Referring next to FIGS. 9 and 10, embodiments of the disclosure may be used in the context of an aircraft manufacturing and service method 900 as shown in FIG. 9 and an aircraft 1000 as shown in FIG. 10. During pre-production, exemplary method 900 may include specification and design 902 of the aircraft 1000 and material procurement 904. During production, component and subassembly manufacturing 906 and system integration 908 of the aircraft 1000 takes place. Thereafter, the aircraft 1000 may go through certification and delivery 910 in order to be placed in service 912. While in service by a customer, the aircraft 1000 may be scheduled for routine maintenance and service 914 (which may also include modification, reconfiguration, refurbishment, and so on).

Each of the processes of method 900 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 10, the aircraft 1000 produced by exemplary method 900 may include an airframe 1004 with a plurality of systems 1002 and an interior 1006. Examples of high-level systems 1002 include one or more of a propulsion system 1008, an electrical system 1010, a hydraulic system 1012, and an environmental system 1014. Any number of other systems may be included. Although an aerospace example is shown, the principles of the invention may be applied to other industries, such as the automotive industry.

The apparatus embodied herein may be employed during any one or more of the stages of the production and service method 900. For example, components or subassemblies corresponding to production process 906 may be fabricated or manufactured in a manner similar to components or subassemblies produced while the aircraft 1000 is in service. Also one or more apparatus embodiments may be utilized during the production stages 906 and 908, for example, by substantially expediting assembly of or reducing the cost of an aircraft 1000. Similarly, one or more apparatus embodiments may be utilized while the aircraft 1000 is in service, for example and without limitation, to maintenance and service 914.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A system for resin thickness measurement, comprising:
    a holding fixture configured to match a contour of a composite part in which a thickness of resin is to be measured;
    a plurality of infrared measurement sensors in said holding fixture;
    a computer-based data acquisition system interfacing with said plurality of infrared measurement sensors; and
    calibration software supporting said data acquisition system.

2. The system for resin thickness measurement of claim 1 wherein said plurality of infrared measurement sensors is arranged in a one-dimensional line array.

3. The system for resin thickness measurement of claim 1 wherein said plurality of infrared measurement sensors is arranged in a two-dimensional grid array.

4. The system for resin thickness measurement of claim 1 wherein each of said plurality of infrared measurement sensors is adapted to emit an infrared beam having a wavelength of from about 900 nm to about 1700 nm.

5. The system for resin thickness measurement of claim 1 wherein said holding fixture is configured to match a generally planar contour of the composite part.

6. The system for resin thickness measurement of claim 1 wherein said holding fixture is configured to match a generally convex contour of the composite part.

7. The system for resin thickness measurement of claim 1 wherein said holding fixture is configured to match a generally concave contour of the composite part.

8. The system for resin thickness measurement of claim 1 wherein said data acquisition system is adapted to collimate resin thickness data at each measurement sensor location into a single two-dimensional map.

9. A system for resin thickness measurement, comprising:
    a holding fixture having a measuring surface configured to match a contour of a composite part wherein a thickness of resin is to be measured;
    a plurality of infrared measurement sensors in said holding fixture and interfacing with said measuring surface;
    a computer-based data acquisition system interfacing with said plurality of infrared measurement sensors; and
    calibration software supporting said data acquisition system and adapted to correlate a level of absorbance of infrared energy at each of said plurality of infrared measurement sensors to a known calibration for resin thickness.

10. The system for resin thickness measurement of claim 9 wherein said plurality of infrared measurement sensors is arranged in a one-dimensional line array.

11. The system for resin thickness measurement of claim 9 wherein said plurality of infrared measurement sensors is arranged in a two-dimensional grid array.

12. The system for resin thickness measurement of claim 9 wherein each of said plurality of infrared measurement sensors is adapted to emit an infrared beam having a wavelength of from about 900 nm to about 1700 nm.

13. The system for resin thickness measurement of claim 9 wherein said measuring surface of said holding fixture is configured to match a generally planar contour of the composite part.

14. The system for resin thickness measurement of claim 9 wherein said measuring surface of said holding fixture is configured to match a generally convex contour of the composite part.

15. The system for resin thickness measurement of claim 9 wherein said measuring surface of said holding fixture is configured to match a generally concave contour of the composite part.

16. The system for resin thickness measurement of claim 9 wherein said data acquisition system is adapted to consolidate resin thickness data at each measurement sensor location into a single two-dimensional image.

17. A method for resin thickness measurement, comprising the steps of:
    configuring a holding fixture to match a contour of a composite part in which a thickness of resin is to be measured and providing an array of infrared measurement sensors in the holding fixture; positioning the holding fixture over a composite structure comprising a resin;
    exposing the resin of the composite structure to near infrared energy at each of said infrared measurement sensors;
    detecting a level of absorbance of infrared energy at each of said infrared measurement sensors; and
    correlating a level of absorbance from each of said infrared measurement sensors to a known calibration for resin thickness.

18. The method of claim 17 wherein said exposing a surface of the composite structure to near infrared energy at each of said infrared measurement sensors comprises exposing a surface of the composite structure to near infrared energy having a wavelength of from about 900 nm to about 1700 nm at each of said infrared measurement sensors.

19. The method of claim 17 wherein said known calibration for resin thickness is based on multivariate spectral analysis of infrared absorbance, multiple peak heights of infrared absorbance or single peak height of infrared absorbance.

20. The method of claim 17 further comprising consolidating resin thickness data at each of said infrared measurement sensors into a single two-dimensional image.

21. The method of claim 17 further comprising forming a two-dimensional map by moving an array of IR sensors along the surface of the part.

* * * * *

UNITED STATES PATENT AND TRADEMARK OFFICE
CERTIFICATE OF CORRECTION

PATENT NO. : 8,338,787 B1  
APPLICATION NO. : 13/151147  
DATED : December 25, 2012  
INVENTOR(S) : Shelley et al.

Page 1 of 1

It is certified that error appears in the above-identified patent and that said Letters Patent is hereby corrected as shown below:

Title Page, Item (75) Inventors, should read

-- (75) Inventors: Paul H. Shelley, Lakewood, WA (US);
Gregory J. Werner, Puyallup, WA (US);
Paul G. Vahey, Seattle, WA (US); Wes W. Quigley, Auburn, WA (US) --.

Signed and Sealed this
Third Day of May, 2016

Michelle K. Lee
*Director of the United States Patent and Trademark Office*